United States Patent
Ronald (10) Patent No.: US 7,041,050 B1
(45) Date of Patent: May 9, 2006

(54) SYSTEM FOR PERFORMING A SURGICAL PROCEDURE INSIDE A BODY

(75) Inventor: Timothy R. Ronald, Clarence, NY (US)

(73) Assignee: Ronald Medical Ltd., Clarence, NY (US)

( * ) Notice: Subject to any disclaimer, the term of this patent is extended or adjusted under 35 U.S.C. 154(b) by 65 days.

(21) Appl. No.: 10/893,793

(22) Filed: Jul. 19, 2004

(51) Int. Cl.
  *A61B 1/00* (2006.01)
(52) U.S. Cl. .................. 600/104; 600/114; 600/121; 600/123; 600/125; 604/164.11; 604/264
(58) Field of Classification Search .............. 600/104, 600/114, 121, 123–125, 118; 604/164.11, 604/264
See application file for complete search history.

(56) References Cited

U.S. PATENT DOCUMENTS

| 4,550,715 A | * | 11/1985 | Santangelo et al. | 600/114 |
| 4,610,242 A | * | 9/1986 | Santangelo et al. | 600/114 |
| 5,267,977 A | * | 12/1993 | Feeney, Jr. | 604/198 |
| 6,695,774 B1 | * | 2/2004 | Hale et al. | 600/173 |
| 6,743,168 B1 | * | 6/2004 | Luloh et al. | 600/167 |
| 6,761,684 B1 | * | 7/2004 | Speier | 600/121 |
| 2005/0245875 A1 | * | 11/2005 | Restelli et al. | 604/164.01 |

* cited by examiner

*Primary Examiner*—Beverly M. Flanagan
*Assistant Examiner*—Matthew J. Kasztejna (57) ABSTRACT

A surgical system comprising a cannula for an elongate surgical tool that enables a physician to operate on a surgical site within a body from outside the body is described. The cannula supports a pin that is locked and unlocked from a J-shaped channel provided in the sidewall of a sheath for a surgical tool. The sheath prevents the surgical tool, such as a scalpel, from cutting the cannula as it is moved there through to the surgical site. The surgical tool, in turn, is provided with a second J-shaped channel that engages with a pin supported by the sheath for locking and unlocking the tool there from to enable a physician to perform the surgical procedure. One surgical tool is interchangeable with another for performing different tasks at the surgical site during the procedure.

19 Claims, 8 Drawing Sheets

SYSTEM FOR PERFORMING A SURGICAL PROCEDURE INSIDE A BODY

BACKGROUND OF THE INVENTION

The present invention generally relates to a medical system for performing a surgical procedure. More particularly, the medical system comprises a cannula for an elongate surgical tool that enables a physician to operate on a surgical site within a body from outside the body. One surgical tool is interchangeable with another for performing different tasks at the surgical site during the procedure.

SUMMARY OF THE INVENTION

A surgical system is described for operating at a surgical site virtually anywhere inside a body. Examples include the brain, chest, abdomen, a limb, and the like. The system comprises a variety of surgical tools that are supported at the end of a tool rod. The surgical tool and the tool rod are locked inside a sheath for moving to the surgical site through an elongate and flexible cannula. The tool rod and sheath are each provided with J-shaped channels that cooperate with locking pins supported by the sheath and cannula, respectively. The cooperating locking pins/J-shaped channels serve as structures for locking and unlocking the surgical tool inside the sheath and the sheathed tool inside the cannula.

To perform a surgical procedure, the tool rod supporting the surgical tool is locked inside the sheath by manipulating the tool rod until the sheath's locking pin resides in a terminus of the tool rod's J-shaped channel. The surgical tool locked inside the sheath is then moved through the cannula to a location proximate the surgical site. The sheath helps prevent the surgical tool, for example a scalpel, from cutting the inside of the cannula during this movement.

The sheath is then locked inside the cannula by manipulating the tool rod/sheath assembly until the cannula's locking pin resides in a terminus of the sheath's J-shaped channel. Next, the tool rod is manipulated in a reverse manner to free it from the sheath by unlocking the sheath's locking pin from the tool rod's J-shaped channel. The tool rod in now moved out of the sheath and the cannula to perform a surgical task. Once that is completed, the tool rod is retracted and locked inside the sheath, locked inside the cannula. The tool rod/sheath assembly is then unlocked from the cannula and removed there from. Another surgical tool, such as a hypodermic needle at the end of another tool rod is then locked inside the sheath. This assembly is then moved into the cannula to a position adjacent to the surgical site, and the procedure is repeated. This continues until the surgical procedure is completed.

Movement of the tool rod and the tool rod/sheath assembly can be by gross manipulation by hand or computer controlled for fine movements. This latter case is particularly desired in moving the tool rod and surgical tool out of the sheath and cannula to perform the operation at the surgical site.

The cannula is also provided with auxiliary functions such as air pressure, vacuum pressure, an illumination light and camera.

These and other objects of the present invention will become increasingly more apparent to those skilled in the art by reference to the following description and the appended drawing.

DETAILED DESCRIPTION OF THE PREFERED EMBODIMENTS

Figure 1:
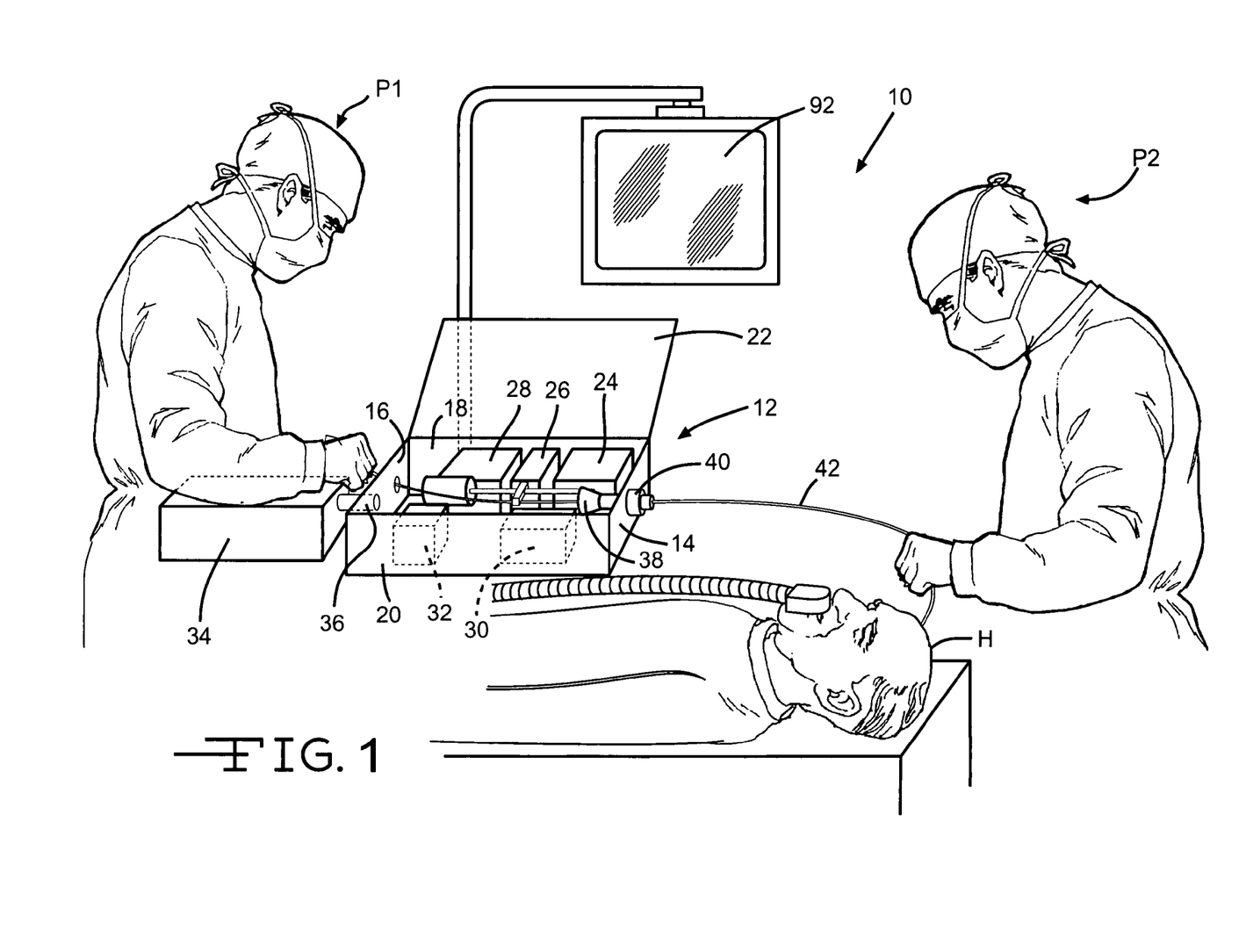
FIG. 1 is a schematic view showing two physicians P1 and P2 operating on a patient using a surgical system 10 according to the present invention.
Figure 2:
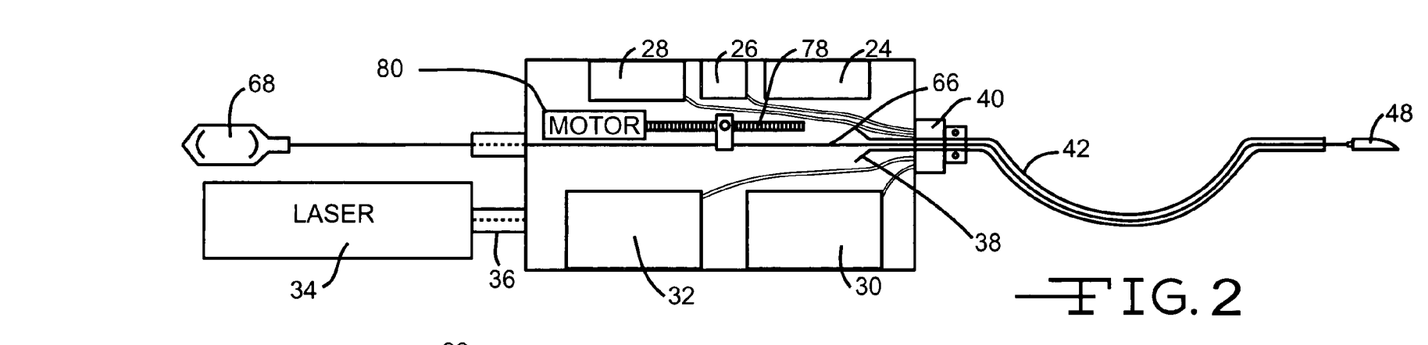
FIG. 2 is a schematic view of the surgical system 10 provided with a scalpel 48

Referring now to the drawings, FIG. 1 shows a first physician P1 assisted by a second physician P2 in performing a surgical procedure on the head H of a patient using a surgical system 10 according to the present invention. The surgical system 10 enables the physicians to operate at a surgical site virtually anywhere inside the patient's body via an incision, vein or artery. In the drawing, the physicians are operating on the patient's head, but this is by way of example only. It is within the scope of the invention that the surgical site can include those in the chest, abdomen, legs, arms, and the like.

As more clearly shown in FIGS. 1 to 8, the surgical system 10 comprises a cabinet 12 comprising spaced apart end walls 14 and 16 extending to opposed sidewalls 18 and 20. Sidewall 18 supports a lid 22 hinged thereto for closing the cabinet. The cabinet contains various components for the surgical system including an air pump 24, a vacuum pump 26, a light source 28, and an electrical power source 30, and a camera 32. A laser 34 resides outside the cabinet 12 with a light conduit 36 communicating through cabinet end wall 16. A funnel-shaped member 38 is housed inside the cabinet 12 supported through end wall 14 by a nut 40. The funnel 38 leads to a cannula 42 having a length sufficient to pass through a surgical opening in the patient's head H and reside adjacent to a surgical site (not shown). The cannula 42 enables a variety of surgical tools to be moved to the surgical site, one after another, for performing the procedure without removing the cannula from the body.

In particular, the surgical system comprises the cannula 42, an inner sheath 44, and a surgical tool 46. The cannula 42 serves as a conduit for the sheath 44. In turn, the sheath 44 houses the surgical tool, such as the scalpel 48 shown in FIG. 5. The cannula 42, sheath 44 and surgical tool 46 are of a moderately flexible, polymeric material and the conduit 42 and surgical tool 46 have a length that enables the physician to manipulate their proximal ends from outside the body while their distal ends are at a surgical site. The sheath 42 is of a much shorter length and only needs to be long enough to cover the tool, for example scalpel 48, so that the tool does not cut the cannula 42 as it is moved to and from the surgical site.

The sheath 44 is received in the cannula 42 and comprises a cylindrically shaped wall 44A extending between a proximal end 50A closest to the surgeon and a distal end 50B. A bore 52 extends through the sheath 44 in communication with the proximal and distal ends 50A, 50B thereof. The bore 52 is aligned along the longitudinal axis of the sheath 44 and comprises a first cylindrically shaped bore portion 52A and a second cylindrically shaped bore portion 52B. The first bore portion 52A extends from the proximal end 50A part way along the length of the sheath 44 to the second bore portion 52B, which extends the remainder of the body length to the distal end 50B. The first bore portion 52A is of a smaller diameter than the second bore portion 52B. The outer surface 44B of the sheath wall 44A at the second bore portion 52B is provided with a J-shaped channel 54 recessed therein.

Figure 5:
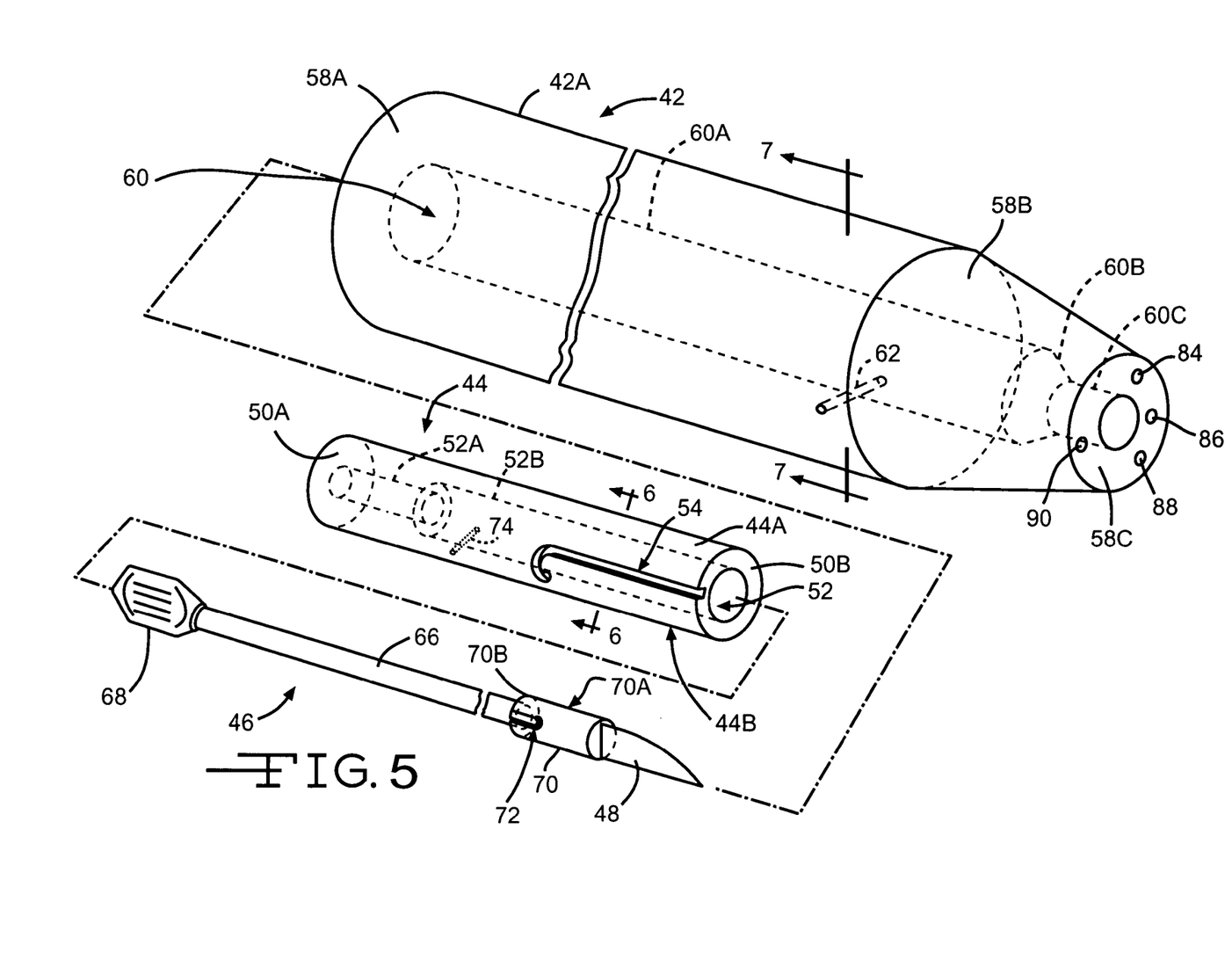
FIG. 5 is an exploded view of a surgical tool 46 comprising the scalpel 48 of FIG. 2 for housing in a sheath 44 that is then housed in a cannula 42 for movement is a surgical site.
Figure 6:
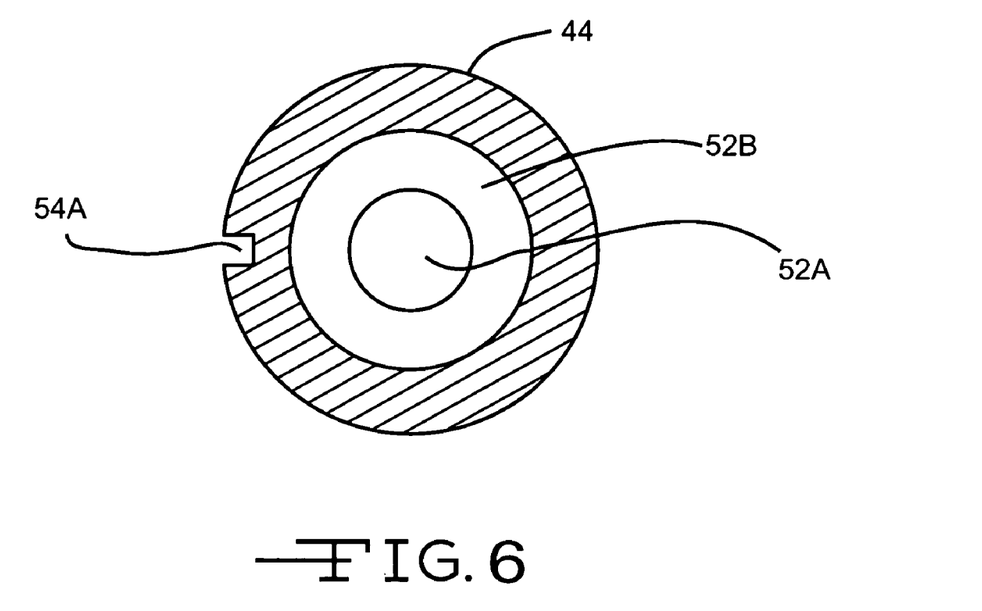
FIG. 6 is a cross-sectional view along line 6—6 of FIG. 5.
Figure 7:
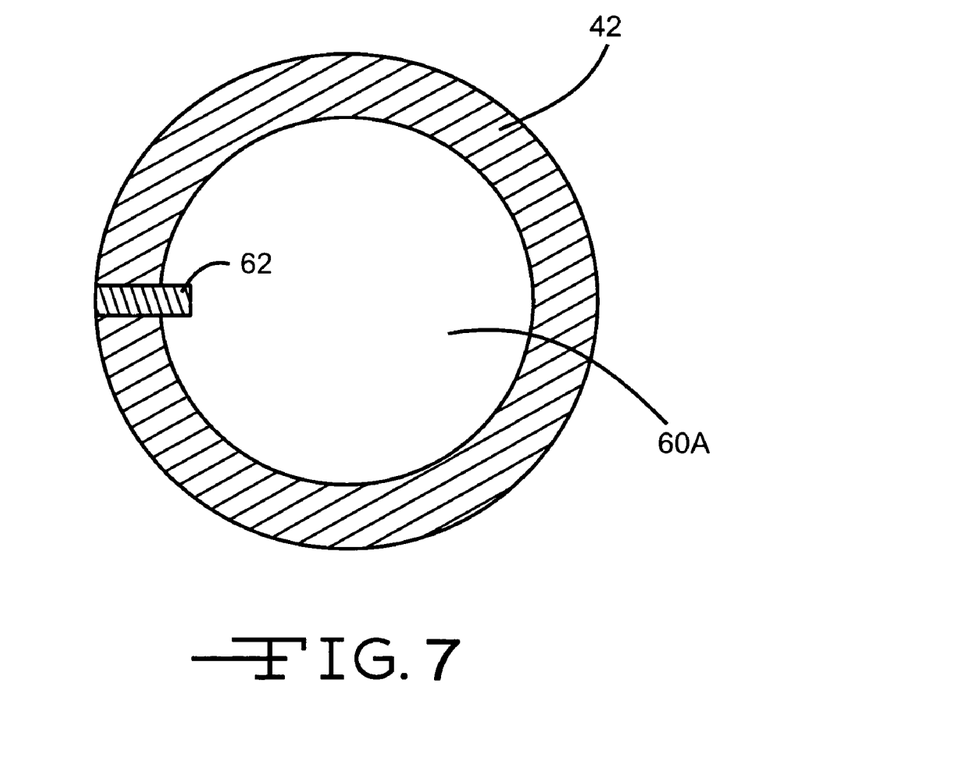
FIG. 7 is a cross-sectional view along line 7—7 of FIG. 5.
Figures 8, 9:
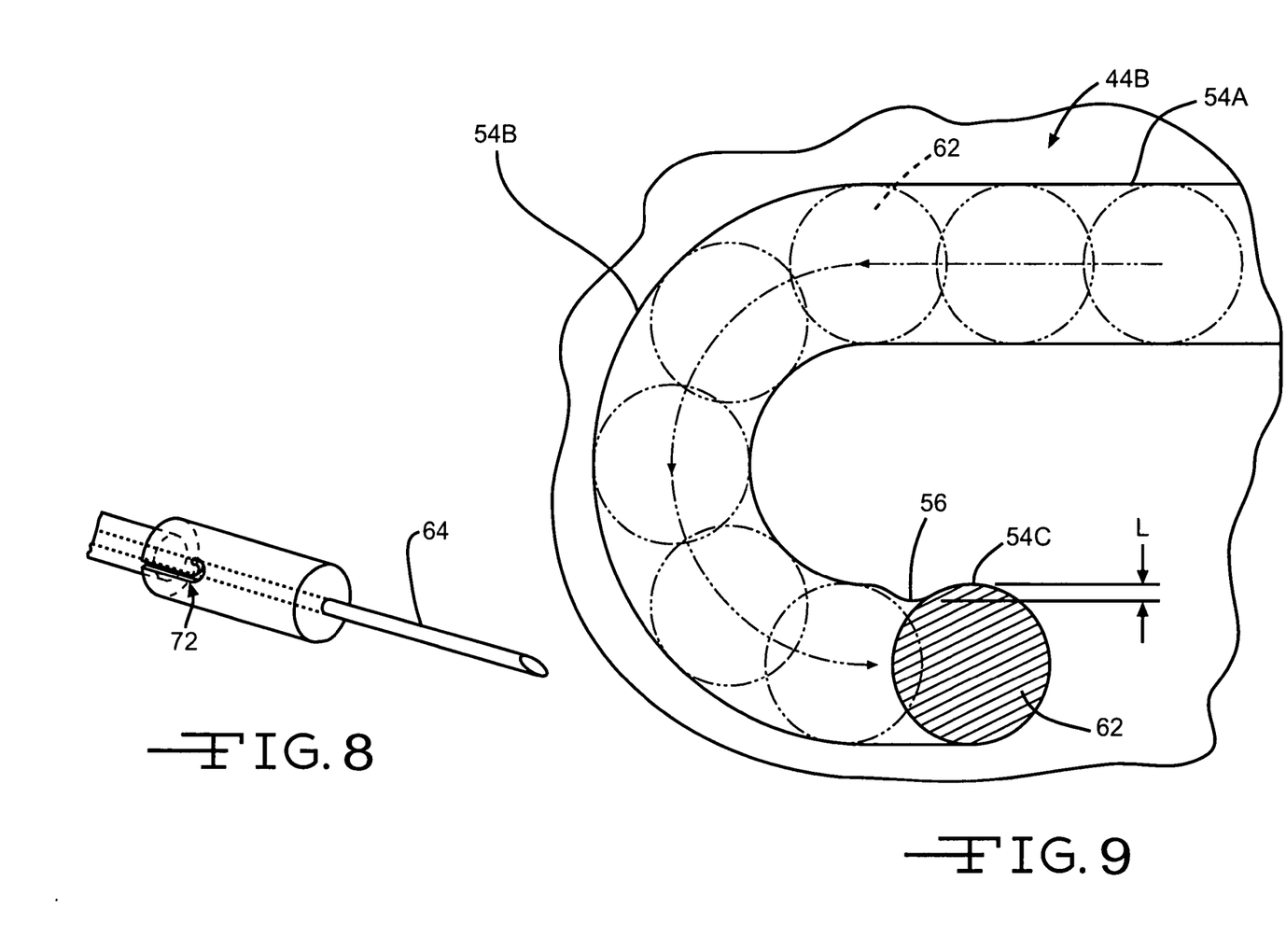
FIG. 8 is a perspective view of surgical tool comprising a hypodermic needle 64 useful with the present surgical system 10.
FIG. 9 is an enlarged, schematic view of the movement the sheath 44 being moved relative to the pin 62 supported by the cannula 42 to lock the sheath inside the cannula.

As clearly shown in the enlarged view of FIG. 9, this channel comprises a longitudinal portion 54A extending from the distal end 50B of the sheath 44 (FIG. 5) aligned parallel to the longitudinal axis thereof to a radiused portion 54B. The radiused portion 54B curves about the longitudinal axis at a fixed radius therefore to a terminus portion 54C. The terminus portion 54C is aligned parallel to the longitudinal channel portion 54A and terminates spaced from the distal end 50B of the sheath 44 (FIG. 5). The J-shaped channel 54 is of a constant width along the entire extent of the longitudinal portion 54A and the radiused portion 54B. However, a protrusion 56 extends into the channel 54 and delineates the radiused portion 54B from the terminus portion 54C. The protrusion 56 is of a height indicated by "L" in the drawing.

Referring to FIGS. 5, 7, 10, 12 and 13, the cannula 42 comprises a cylindrically shaped cannula wall 42A that extends from a proximal end 58A to a frusto-conically shaped nose portion 58B. The nose portion tapers downwardly and inwardly to the distal end 58C of the cannula. The cannula 42 includes a bore 60 comprising a first cylindrically shaped bore portion 60A extending from the proximal cannula end 58A to the cannula nose portion 58B. There, first bore portion 60A meets a frusto-conically shaped bore portion 60B tapering downwardly and inwardly to a second cylindrically shaped bore portion 60C extending to the distal end 58C of the cannula 42.

The cannula wall 42A supports a pin 62 that is flush with the outer surface thereof. A portion of the pin 62 extends into the first bore portion 60A aligned radially along the longitudinal axis of the cannula 42. The pin 62 has a diameter that fits in the width of the J-shaped channel 54 in a closely spaced relationship. That way, with the sheath 44 housed inside the cannula 42, the pin 62 is alignable with the longitudinal portion 54A of the channel 54. The sheath 44 is then movable relative to the cannula 42 with the channel 54 moving relative to the pin 62 confined therein to lock the sheath 44 inside the cannula 42 when the pin is received in the terminus channel portion 54C (FIG. 9).

Figure 12:
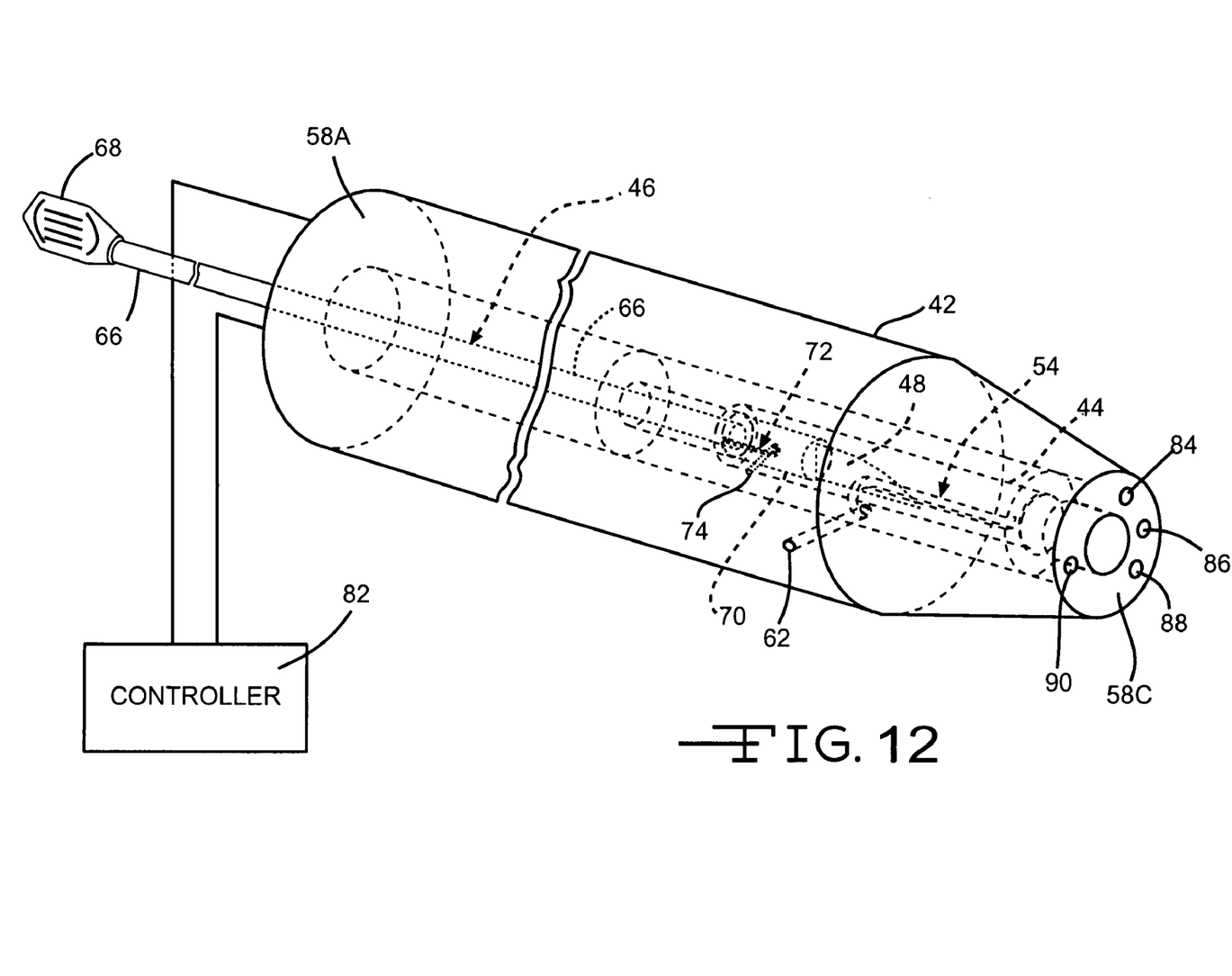
FIG. 12 is a perspective view, partly in phantom, showing surgical tool the 46 comprising the scalpel 48 locked inside the sheath 44, which, in turn is locked inside the cannula 42.
Figure 13:
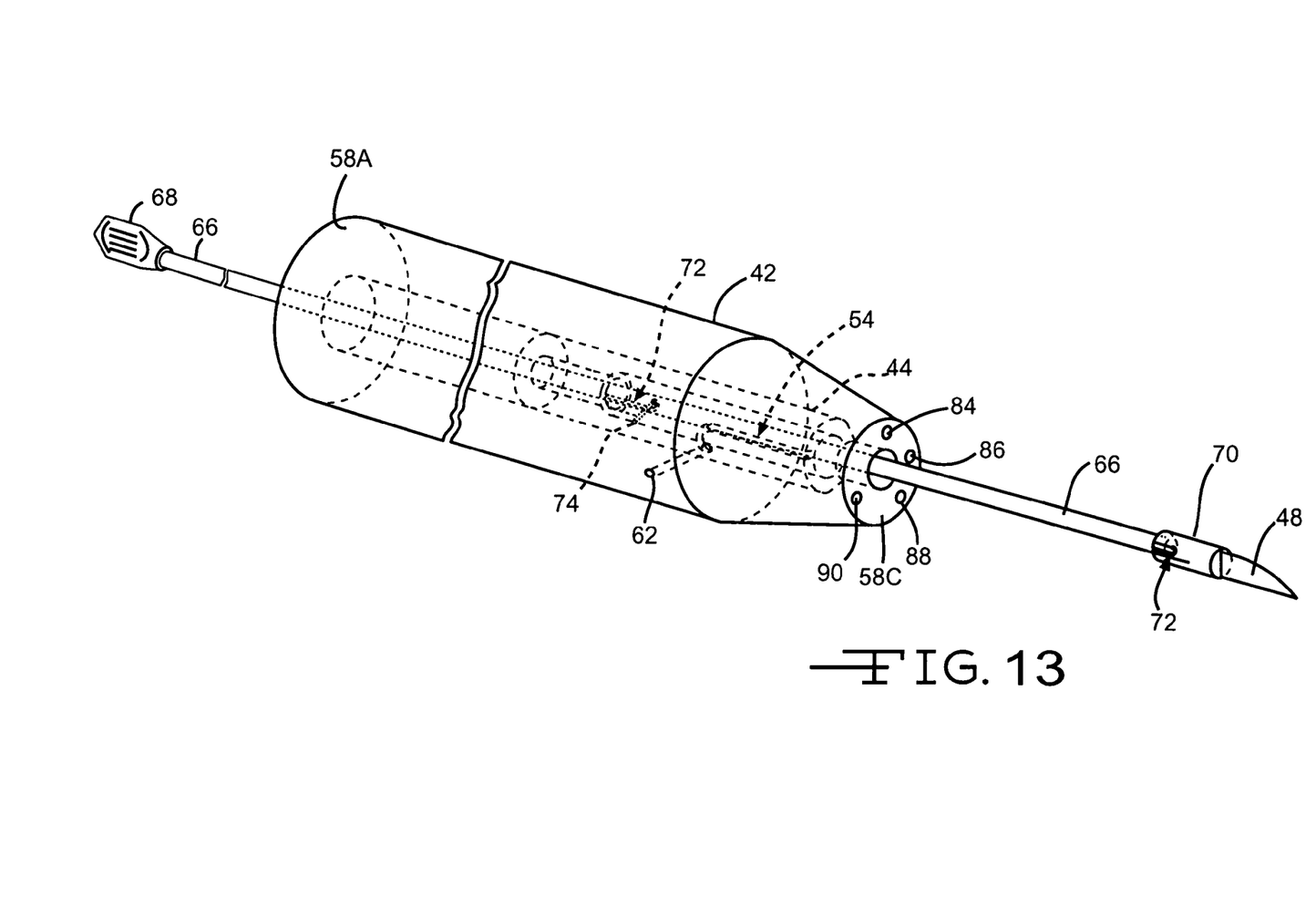
FIG. 13 is a perspective view, partly in phantom, showing the scalpel 48 extending out of the sheath 44 locked inside the cannula 42.

This occurs by moving the distal end 50B of the sheath 44 into the bore 60 of the cannula 42 at the proximal end 58A. As the sheath 44 is moved relative to the cannula 42, the pin 62 is first confined in the longitudinal channel portion 54A with the distal end SOB of the sheath 44 moving toward the tapered nose portion 58B of the cannula. Further relative longitudinal and rotational movement confines the pin 62 in the radiused portion 54B until the pin contacts the protrusion 56. The material of the sheath 44 and, consequently, the protrusion 56 is somewhat resilient. A moderate pushing force is then sufficient to move the pin 62 past the protrusion 56 to reside in the channel terminus portion 54C. In that manner, the sheath 44 is locked relative to the cannula 42 with the distal end 50B of the sheath substantially coplanar with or recessed somewhat inside the distal end 58C of the cannula proximate the tapered nose portion 58B (FIG. 12).

Referring back to FIG. 5, the scalpel 48 of the surgical tool 46 is received in the sheath 44 serving as a housing for the scalpel. The surgical tool can also comprise a hypodermic needle 64 (FIG. 8). Other tools are also contemplated by the present invention.

The surgical tool 46 comprising the scalpel 48 includes a cylindrically shaped tool rod 66 extending between a detachable handle 68 at it proximal end closest to the surgeons and a distal, cylindrically shaped head 70. The head 70 is of a diameter sized to fit inside the second bore portion 52B of the sheath 44 in a closely spaced relationship. The outer surface 70A of the head 70 is provided with a J-shaped channel 72 recessed therein. This channel is similar in construction to the J-shaped channel 54 of the sheath 44, but smaller in size. While not provided with a numerical designation in the drawings, channel 72 also comprises a longitudinal portion extending from a proximal end 70B of the head aligned parallel to the longitudinal axis thereof to a radiused portion. The radiused portion curves about the longitudinal axis at a fixed radius therefore to a terminus portion. The terminus portion is aligned parallel to the longitudinal portion of the channel 72. The J-shaped channel 72 is of a constant width along the entire extent of its longitudinal portion and radiused portion. A protrusion (not shown) extends into the channel and delineates the radiused portion from the terminus portion. This protrusion is similar to the protrusion of the J-shaped channel 54 of sheath 44, but proportionately smaller in size.

Figures 10, 11:
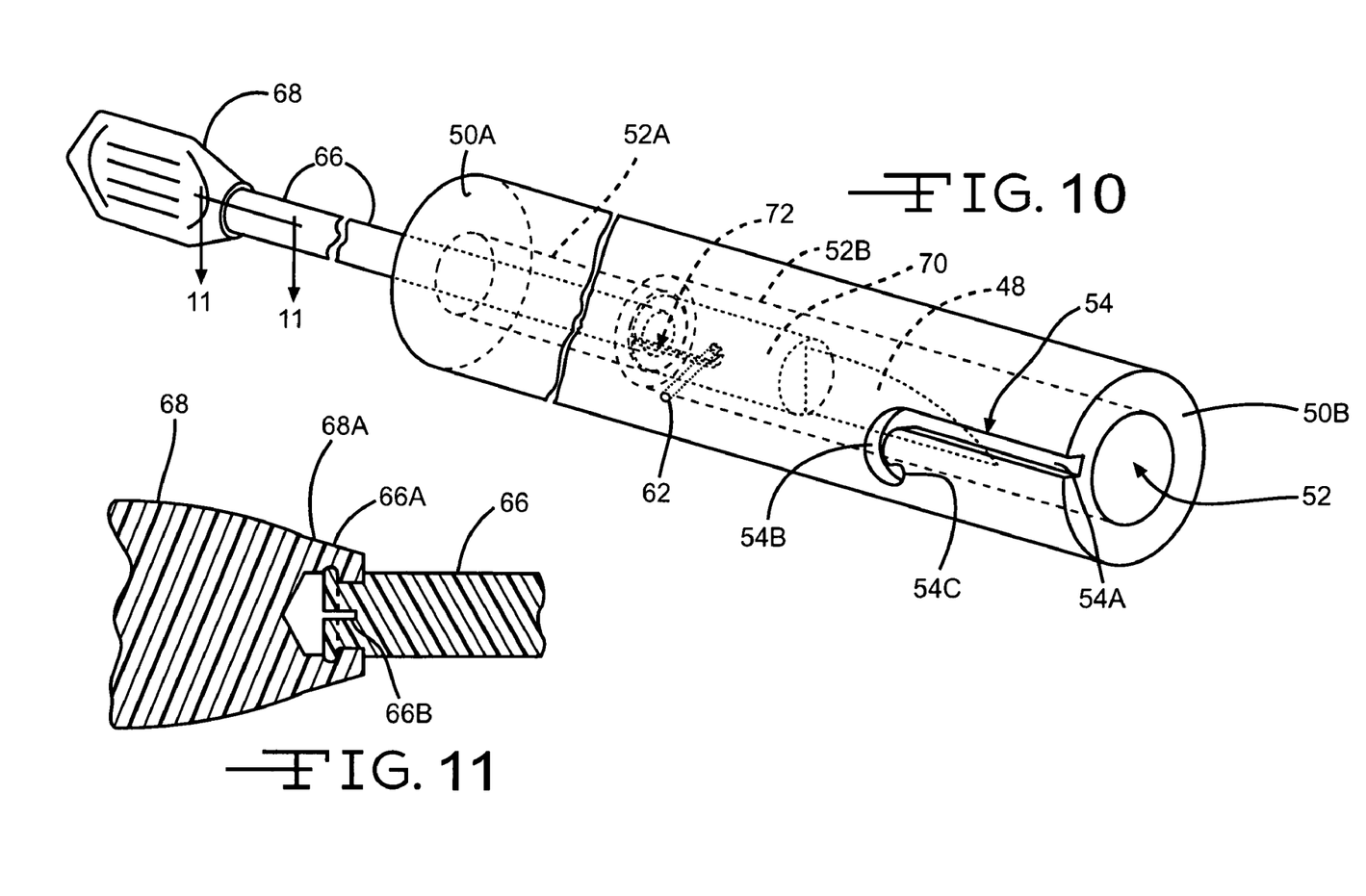
FIG. 10 is a perspective view, partly in phantom, of the tool rod 66 connected to a head 70 supporting a scalpel 48 locked inside the sheath 44.
FIG. 11 is a cross-sectional view along line 11—11 of FIG. 10 of the handle 68 snap fit on the end of the tool rod 66 for the surgical tool 46.

The sheath wall 44A supports a pin 74 flush with an outer surface thereof. A portion of the pin 74 extends into the second bore portion 52B aligned radially along the longitudinal axis of the sheath 44. The pin 74 has a diameter that fits in the width of the J-shaped channel 72 in a closely spaced relationship. That way, with the head 70 and scalpel 48 of the surgical tool 46 housed inside the sheath 44, the pin 74 is alignable with the longitudinal portion of channel 72. This occurs by first removing the handle 68 from the tool rod 66. As shown in FIG. 11, the handle 68 is provided with a flexible yoke 68A that snap fits over an annular protrusion 66A of the tool rod 66. A slot 66B enables the rod 66 to flex somewhat as the yoke snaps on and off of the rod. Then, the yoke 68A nests in a groove on opposite sides of the rod 66. This prevents relative slippage during manipulation.

The annular protrusion 66A of the handle is sized to fit into the first bore portion 52A of the sheath 44. That way, the annular protrusion 66A is moved into the sheath at the distal end 50B passing through the second bore portion 52B and then the first bore portion 52A until it exits the proximal end 50A. As this movement occurs, the longitudinal portion of the channel 72 is aligned with the pin 74. A pulling force on the tool rod 66 causes relative movement of the pin along the longitudinal channel portion with the scalpel 48 moving away from the distal end 50B of the sheath 44. Further relative longitudinal and rotational movement causes the radiused portion of the channel 72 to move relative to the pin 74 until the pin contacts the channel protrusion. The material of the head 70 and, consequently, the protrusion is somewhat resilient. A moderate pushing force is then sufficient to move the protrusion past the pin 74 now residing in the channel terminus portion. In that manner, the tool rod 66 is locked relative to the sheath 44 with the scalpel 48 supported by the head 70 recessed somewhat inside the distal end 50B of the sheath (FIGS. 10 and 12).

In Use

To perform a surgical procedure, a physician first selects the desired surgical tool, such as the surgical tool 46 (FIG. 5) having the tool rod 66 connected to the head 70 supporting the scalpel 48. The tool rod 66 without the handle 68 is then loaded into the distal end 50B of the sheath 44 until the proximal end 70B of the head 70 abuts the constriction of the first bore portion 52A to the second bore portion 52B. This loading movement has previously been described. To facilitate movement of the tool rod 66 past this point, the constriction preferably has a frusto-conical taper funneling down from the large diameter bore 52B to the smaller bore portion 52A sized to fit the annular protrusion 66A of the tool rod.

As this movement occurs, the pin 74 supported by the sheath 44 moves along the longitudinal portion of the J-shaped channel 72 in head 70 until it enters the radiused portion. The tool rod 66 is now rotated, causing the pin 74 to move along the radiused channel until it contacts the protrusion delineating the terminus portion. The tool rod is now pushed forward toward the distal end 50B of the sheath with enough force to cause the pin to move past the protrusion and lock in the terminus portion of the J-shaped channel 72. The tool rod 66 and, consequently, the surgical tool 46 are now locked in place relative to the sheath 44 with the head 70 and scalpel 48 housed therein. The handle 68 is then fitted onto the proximal end of the tool rod 66 extending outwardly from the proximal end 50A of the sheath 44.

Next, the cannula 42 is positioned inside the body with its distal end 58C proximate the surgical site and its proximal end 58A residing outside the body, accessible by the physicians P1 and P2 (FIG. 1). One of the important aspects of the present invention is that movement of the surgical tools, for example scalpel 48 can be either by gross adjustment using the handle 68 at the proximal end of tool rod 66 or it can be computer controlled for more precise adjustments. Gross movement is used to position the sheath 44/surgical tool 46 assembly adjacent to the pin 62 supported by the cannula. More precise movement is needed to lock sheath 44 in the cannula, to unlock the surgical tool 46 from the sheath 44, to use the scalpel 48 for cutting at the surgical site, to re-lock the surgical tool 46 inside the sheath 44 and for unlocking the sheath from the cannula to remove it there from. These movements all require fine adjustments.

As shown in FIGS. 1 to 4, the tool rod 66 is detachably connected to the arm 76 and worm gear 78 of a controller driven motor 80. First, a computerized controller 82 connected to the electrical power source 30 controls movement of the distal end of the cannula through a series of plastic wires (not shown) running the length of the cannula. The wires preferably reside in the cannula sidewall and provide articulation movement of the cannula so that the physicians can guide the distal end 58C thereof to a desired location in the body.

As schematically shown in FIG. 12, the computerized controller 82 also controls actuation of forward, rearward and rotational movement of the tool rod 66. Gross movement is used to first move the distal end SOB (FIG. 10) of the sheath into the proximal end 58A of the cannula until the longitudinal portion 54A of the J-shaped channel 54 is aligned with the pin 62 supported by the cannula 42. Relative longitudinal movement of the tool rod 66 and connected sheath 44 into the cannula 42 continues under the control of the computer driven motor 80 with the longitudinal channel portion 54A traveling along the pin 62 to the beginning of the radiused portion 54B. The sheath 44 (FIG. 12) must now be rotated relative to the cannula 42 until the pin 62 contacts the protrusion 56 (FIG. 9). A pulling force is now applied to the sheath 44 until the pin 62 lodges in the terminus channel portion 54C. The tool rod 66 and sheath 44 are now locked relative to the cannula 42 with the scalpel 48 housed in the sheath. The distal end 50B of the sheath is substantially coplanar, or somewhat recessed inside, with respect to the distal end 58C of the cannula.

Next, the scalpel 48 is unlocked from the sheath 44 by the controller 82 actuated motor 80 using a pulling force applied to the tool rod 66 sufficient to move the protrusion of channel 72 past the pin 74 (FIG. 12). With the pin now confined in the radiused portion. The tool rod 66 is rotated relative to the sheath until the pin 74 is in the longitudinal channel portion. The tool rod 66 is next moved forward with the pin moving along and then free of the longitudinal portion. As this happens, the scalpel 48 exits the distal end 50B of the sheath 44 (FIG. 10) and then the distal end 58C of the cannula 42. The physicians are now able to use the scalpel in performing the surgical procedure.

As shown in FIGS. 1, 2, 5, 12 and 13, the cannula 42 is provided with ports leading to conduits (not shown) provided in the cannula sidewall. Four ports are shown, and they connect to the air pump 24, vacuum pump 26, light 28 and camera 32 contained in the cabinet 12 (FIG. 1). For example, port 84 connects to air pump 24 for delivering air pressure to the surgical site, port 86 connects to vacuum pump for delivering suction pressure, port 88 connects to the light 28 illumination at the surgical site, and port 90 connects to camera for providing real time images of the surgical site on monitor 92. The ports communicate through the sidewall of the cannula 42 to the controller 82 and the respective supplies 24, 26, 28 and 32 located in the cabinet 12.

Figures 3, 4:
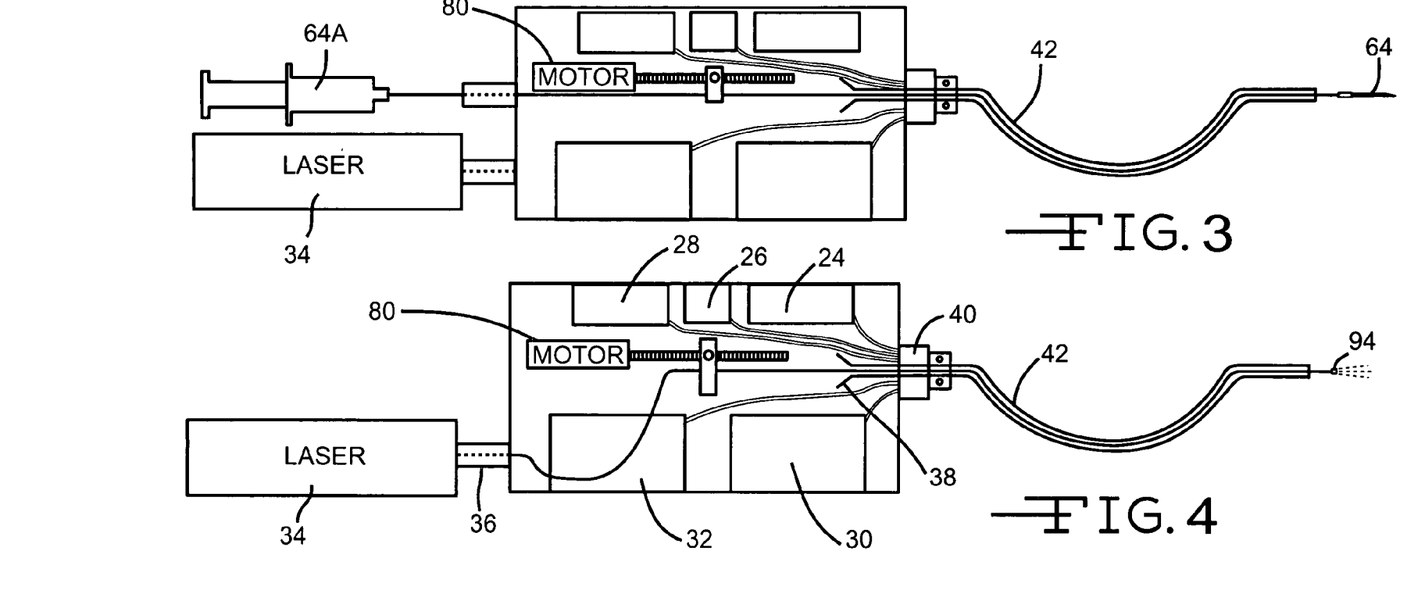
FIG. 3 is a schematic view of the surgical system 10 provided with a needle 64.
FIG. 4 is a schematic view of the surgical system 10 provided with a laser 92.

Then, when the physician is done cutting with the scalpel 48, the tool rod 66 is removed from the surgical site by the controller 82 connected to the motor 80. This is done by retracting the scalpel 48 back into the sheath 44 with relative movement of the pin 74 along the longitudinal portion, then the radiused portion and finally the terminus portion of channel 72 to again house and lock the scalpel inside the sheath. The sheath 44 is then unlocked from the cannula 42. Manipulating the sheath 44 such that the channel terminus portion 54C and protrusion 56 are moved along the pin 62 followed by the radiused portion 54B and the longitudinal portion 54A does this. The motor 82 preferably controls this movement. The tool handle 66 is then disconnected from the motor driven arm 76 and the handle 68 is snapped onto the end of the tool rod to remove the surgical tool 46 housed inside the sheath 44 from the cannula free there from. The handle 68 is now unsnapped from the tool rod 66 and the surgical tool 46 is unlocked from the sheath to un-house the scalpel 48. The surgical tool 46 comprising the scalpel 48 is now replaced by a different surgical tool comprising, for example, the hypodermic needle 64 with its attendant plunger 64A serving as a handle (FIGS. 3 and 8), or one containing a laser light 92 (FIG. 4). The above-described process is then repeated to enable the physician to continue the surgical procedure with the hypodermic needle 64, laser 92, or some other surgical device as well known by those skilled in the art. During any one of these procedures, the physicians have use of the functions provided by the cannula including the air pressure 24, vacuum 26, light 28 and camera 32.

The present invention is not intended to be limited by the described embodiments, but by the herein appended claims.

What is claimed is:

1. A medical system for enabling a physician to operate at a surgical site inside a body, which comprises:
    a) an elongated cannula providing a cannula bore having a first length extending between a distal cannula end and a spaced apart proximal cannula end, wherein the distal cannula end is adapted to reside inside the body adjacent to the surgical site with the proximal cannula end accessible from outside the body;
    b) a sleeve providing a sleeve bore having a second length extending between a distal sleeve end and a spaced apart proximal sleeve end, wherein the sleeve has a first outer surface;
    c) a surgical tool comprising a tool rod having a third length extending between a tool rod head and a spaced apart proximal tool rod end, wherein the tool rod head comprises a proximal head end and a distal head end supporting a surgical tool with the third length enabling the surgical tool to be housed inside the sleeve with the sleeve housing the surgical tool residing inside the cannula adjacent to the distal cannula end positioned adjacent to the surgical site and with the proximal tool end being manipulatable from outside the body adjacent to the proximal cannula end; and
    d) wherein the tool rod head has a second outer surface including a second J-shaped channel and the sleeve supports a second pin extending into the sleeve bore oriented perpendicular to a longitudinal axis thereof, wherein the second pin is matable with the second J-shaped channel to provide for locking and unlocking the surgical tool inside the sleeve.

2. The medical system of claim 1 wherein the first outer surface of the sleeve includes a first J-shaped channel and the cannula supports a first pin extending into the cannula bore oriented perpendicular to a longitudinal axis thereof, wherein the first pin is matable with the first J-shaped channel to provide for locking and unlocking the sleeve inside the cannula.

3. The medical system of claim 2 wherein the first J-shaped channel comprises a first longitudinal channel portion that begins at the distal sleeve end and extends at least part way along the second length to a first radiused portion delineated from a first terminus portion by a first resilient protrusion.

4. The medical system of claim 1 wherein the second J-shaped channel comprises a second longitudinal channel portion that begins at the proximal head end and extends at least part way toward the distal head end supporting the surgical tool to a second radiused portion delineated from a second terminus portion by a second resilient protrusion and wherein the tool rod is manipulatable to cause the second pin to enter the second J-shaped channel and travel there along as the tool rod is moved in an axial direction with respect to the second pin of the sleeve with the tool rod head moving toward the distal sleeve end until the second pin encounters the second radiused portion at which the entire tool rod is manipulatable in the continued axial direction while being rotated until the second pin passed the second resilient protrusion and resides in the second terminus portion to thereby lock the tool rod inside the sleeve.

5. The medical system of claim 1 wherein the proximal tool rod end detachably supports a handle for gross manipulation of the sleeve housing the tool rod locked thereto along the cannula bore to a position adjacent to the distal cannula end.

6. The medical system of claim 1 wherein the proximal end of the tool rod is connectable to a computer controlled motor for fine movement of the sleeve housing the surgical tool into and out of a locked relationship with the cannula and for fine movement of the surgical tool into and out of a locked relationship with the sleeve.

7. The medical system of claim 1 wherein the surgical tool is selected from the group consisting of a scalpel, a hypodermic needle, and a laser.

8. The medical system of claim 1 wherein the cannula comprises a sidewall surrounding the cannula bore with at least one of the group consisting of an illumination light, air pressure, vacuum, and a camera communicating from the distal cannula end through the sidewall to outside the body for actuation by the physician.

9. A method for performing a surgical operation inside a body, comprising the steps of:
    a) providing a medical system, which comprises:
        i) an elongated cannula providing a cannula bore having a first length extending between a distal cannula end and a spaced apart proximal cannula end, wherein the distal cannula end is adapted to reside inside the body adjacent to the surgical site with the proximal cannula end accessible from outside the body;
        ii) a sleeve providing a sleeve bore having a second length extending between a distal sleeve end and a spaced apart proximal sleeve end, wherein the sleeve has a first outer surface including a first J-shaped channel that is matable with a first pin supported by the cannula and extending into the cannula bore oriented perpendicular to a longitudinal axis thereof to provide for locking and unlocking the sleeve inside the cannula; and
        iii) a surgical tool comprising a tool rod having a third length extending between a tool rod head and a spaced apart proximal tool rod end, wherein the tool rod head comprises a proximal head end and a distal head end supporting a surgical tool with the third length enabling the surgical tool to be housed inside the sleeve with the sleeve housing the surgical tool residing inside the cannula adjacent to the distal cannula end positioned adjacent to the surgical site with the proximal tool end being manipulatable from outside the body adjacent to the proximal cannula end, and wherein the tool rod head has a second outer surface including a second J-shaped channel that is mateable with a second pin supported by the sleeve and extending into the sleeve bore oriented perpendicular to a longitudinal axis thereof to provide for locking and unlocking the surgical tool inside the sleeve; and
    b) positioning the cannula inside the body such that the distal cannula end resides adjacent to the surgical site and the proximal cannula end is accessible from outside the body;

c) locking the surgical tool inside the sleeve by manipulating the tool rod so that the second pin of the sleeve is in the second J-shaped channel of the tool rod, thereby forming a surgical tool/sleeve assembly;

d) moving the surgical tool/sleeve assembly into the proximal cannula end and along the cannula bore to lock the sleeve inside the cannula with the first pin of the cannula in the first J-shaped channel of the sleeve; and e) unlocking the tool rod and the surgical tool from the sleeve and then moving the surgical tool out of the distal sleeve end and the distal cannula end to perform a surgical function on the body.

10. The method of claim 9 including providing the first J-shaped channel comprising a first longitudinal channel portion beginning at the distal sleeve end and extending at least part way along the second length to a first radiused portion delineated from a first terminus portion by a first resilient protrusion, wherein with the surgical tool/sleeve assembly locked inside the cannula, the first pin of the cannula is confined in the first terminus portion of the sleeve.

11. The method of claim 9 including providing the second J-shaped channel comprising a second longitudinal channel portion beginning at the proximal head end and extending to a second radiused portion delineated from a second terminus portion by a second resilient protrusion, wherein with the surgical tool locked inside the sleeve, the second pin of the sleeve is confined in the second terminus portion of the tool head.

12. The method of claim 9 including providing a handle detachably connectable to the proximal tool rod end and manipulating the handle to move the sleeve housing the tool rod locked thereto along the cannula bore to a position adjacent to the distal cannula end.

13. The method of claim 9 including connecting the proximal end of the tool rod to a computer controlled motor for fine movement of the sleeve housing the surgical tool into and out of the locked relationship with the cannula and for fine movement of the surgical tool into and out of the locked relationship with the sleeve.

14. The method of claim 9 including the cannula further comprising a sidewall surrounding the cannula bore having at least one of the group consisting of an illumination light, air pressure, vacuum, and a camera communicating from the distal cannula end through the sidewall to the proximal cannula end for use during the surgical operation.

15. The method of claim 9 wherein the second J-shaped channel comprises a second longitudinal channel portion beginning at the proximal head end and extending at least part way toward the distal head end supporting the surgical tool to a second radiused portion delineated from a second terminus portion by a second resilient protrusion.

16. The method of claim 9 wherein with the tool rod head and surgical tool disposed inside the sleeve, the second pin extends into the second J-shaped channel of the tool rod head.

17. The method of claim 9 wherein the cannula comprises a sidewall surrounding the cannula bore with at least one of the group consisting of an illumination light, air pressure, vacuum, and a camera communicating from the distal cannula end through the sidewall to outside the body for actuation by the physician.

18. The method of claim 9 including after the surgical function is completed, the further steps of:

a) moving the tool rod and the surgical tool back into being housed inside the sleeve and locking them therein by manipulating the tool rod so that the second pin of the sleeve is in the second J-shaped channel of the tool rod to once again provide the surgical tool/sleeve assembly with the sleeve locked inside the cannula;

b) unlocking the sleeve from the cannula with the first pin of the cannula releasing from the first J-shaped channel of the sleeve and then removing the surgical tool/sleeve assembly from the proximal cannula end and along the cannula bore; and c) removing the cannula from the surgical site and the body.

19. A medical system for enabling a physician to operate at a surgical site inside a body, which comprises:

a) an elongated cannula providing a cannula bore having a first length extending between a distal cannula end and a spaced apart proximal cannula end, wherein the distal cannula end is adapted to reside inside the body adjacent to the surgical site with the proximal cannula end accessible from outside the body;

b) a sleeve providing a sleeve bore having a second length extending between a distal sleeve end and a spaced apart proximal sleeve end;

c) a surgical tool comprising a tool rod having a third length extending between a tool rod head and a spaced apart proximal tool rod end, wherein the tool rod head comprises a proximal head end and a distal head end supporting a surgical tool with the third length enabling the surgical tool to be housed inside the sleeve with the sleeve housing the surgical tool residing inside the cannula adjacent to the distal cannula end positioned adjacent to the surgical site and with the proximal tool end being manipulatable from outside the body adjacent to the proximal cannula end;

d) wherein the sleeve has a first outer surface including a first J-shaped channel and the cannula supports a first pin extending into the cannula bore oriented perpendicular to a longitudinal axis thereof, wherein the first pin is matable with the first J-shaped channel to provide for locking and unlocking the sleeve inside the cannula; and e) wherein the tool rod head has a second outer surface including a second J-shaped channel and the sleeve supports a second pin extending into the sleeve bore oriented perpendicular to a longitudinal axis thereof, wherein the second pin is matable with the second J-shaped channel to provide for locking and unlocking the surgical tool inside the sleeve.

* * * * *